United States Patent [19]
Dimaio et al.

[11] Patent Number: 5,990,104
[45] Date of Patent: Nov. 23, 1999

[54] POLYCYCLIC ALCALOID-DERIVATIVES AS NMDA-RECEPTOR ANTAGONISTS

[75] Inventors: John Dimaio, Montreal; Dilip M. Dixit, Roxboro, both of Canada

[73] Assignee: Biochem Pharma, Inc., Laval, Canada

[21] Appl. No.: 08/981,935

[22] PCT Filed: Jul. 12, 1996

[86] PCT No.: PCT/CA96/00468

§ 371 Date: Mar. 25, 1998

§ 102(e) Date: Mar. 25, 1998

[87] PCT Pub. No.: WO97/03929

PCT Pub. Date: Feb. 6, 1997

[30] Foreign Application Priority Data

Jul. 14, 1995 [GB] United Kingdom .................... 9514448

[51] Int. Cl.$^6$ .................................................. A61K 31/00
[52] U.S. Cl. .......................... 514/212; 514/213; 514/295; 514/411; 514/430; 514/431; 514/437; 514/438; 514/443; 514/454; 514/450; 514/451; 514/455; 514/461; 514/468; 548/400; 548/434; 540/576; 540/581; 546/97; 549/12; 549/26; 549/27; 549/28; 549/43; 549/46; 549/48; 549/354; 549/356; 549/386; 549/459
[58] Field of Search ..................................... 514/646, 656, 514/657, 660, 661, 212, 213, 295, 411, 430, 431, 437, 438, 443, 454, 450, 451, 455, 461, 468; 549/12, 26, 27, 28, 43, 46, 48, 354, 356, 386; 540/459, 576, 581; 546/97; 548/400, 434

[56] References Cited

U.S. PATENT DOCUMENTS 3,836,670 9/1974 Freed et al. .............................. 424/330
4,957,909 9/1990 Abou-Gharbia et al. .................. 514/75

OTHER PUBLICATIONS

Malis et al., "Animal Pharmacology of Wy–16,225, A New Analgesic Agent", *The Journal of Pharmacology and Experimental Therapeutics*, vol. 194, No. 3, pp. 488–498, (1975).

A.A. Farooqui & L.A. Horrocks, "Brain Research Reviews" 16, Excitatory amino acid receptors, neural membrane phospholipid metabolism and neurological disorders, 1991, pp. 171–191.

A.B. MacDermott & N. Dale, "TINS" 10 (7), Receptors, ion channels and synaptic potentials underlying the integrative actions of excitatory amino acids, 1987, pp. 280–284.

S.I. Said, H.I. Berisha & H. Pakbaz, "Neuroscience" 65 (4), N–Methly–D–Aspartate Receptors Outside The The Central Nervous System: Activation Causes Lung Injury That is Mediated by Nitric Oxide Synthesis and Prevented by Vasoactive Intestinal Peptide, 1995, pp. 943–946.

J.W. Olney, "Annu. Rev. Pharmacol. Toxicol." 30, Excitotoxic Amino Acids and Neuropsychiatric Disorders, 1990, pp. 47–71.

A.C. Foster, R. Gill, L.L. Iversen, J.A. Kemp, E.H.F. Wong & G.N. Woodruff, "Current and Future Trends in Anticonvulsant, Anxiety, and Stroke Therapy", Therapeutic Potential of NMDA Receptor Antagonists as Neuroprotective Agents, 1990, pp. 301–329.

M.A. Rogawski & R.J. Porter, "Pharmacological Reviews", 42(3), Antiepileptic Drugs: Pharmacological and Clinical Efficacy with Consideration of Promising Developmental Stage Compounds, 1990, pp. 222–286.

J.W. Downing, J.G. Brock–Utne, A. Barclay and I.L. Schwegmann, "Brit J. Anaesth", WY 16225 (Dezocine), A New Synthetic Opiate Agonist–Antagonist and Potent Analgesic: Comparison With Morphine for Relief of Pain After Lower Abdominal Surgery, 1981, pp. 59–64.

M.E. Freed, J.R. Potoski, E.H. Freed, G.L. Conklin & J.L. Malis, "Journal of Medicinal Chemistry" 16(6), Bridged Aminotetralins as Novel Potent Analgesic Substances, 1973, pp. 595–599.

W. Koek & F.C. Colpaert, "The Journal of Pharmacology and Experimental Therapeutics" 252(1), Selective Blockade of N–Methyl–D–Aspartate (NMDA)–Induced Convulsions by NMDA Antagonists and Putative Glycine Antagonists: Relationship with Phencyclidine–Like Behavioral Effects, 1990, pp. 349–357.

(List continued on next page.)

*Primary Examiner*—Cecilia J. Tsang
*Assistant Examiner*—C. Delacroix-Muirheid
*Attorney, Agent, or Firm*—Foley & Lardner

[57] ABSTRACT

Polycyclic alkaloids of formula (I), wherein $R_1$ is H, $C_{1-6}$ alkyl, or $C_{6-12}$ aryl optionally substituted with polar groups; $R_2$ and $R_3$ are independently H, OH, $C_{1-6}$ alkyl, —C(NH)—$NH_2$, a positively charged group, or $C_{7-13}$ aralkyl optionally substituted with $NH_2$, OH, $C_{1-6}$ alkyl, or halogen; or $R_2$ and $R_3$ together form a 5 to 6 member ring optionally incorporating a heteroatom; $R_4$ is H, $C_{1-6}$ alkyl, $OR_6$, $SR_6$, or $N(R_6)_2$, wherein each $R_6$ is independently H, $C_{1-3}$ alkyl; X ix O, S, SO, $SO_2$, or N—$R_5$, wherein each $R_5$ is independently H, $C_{1-6}$ alkyl, or $C_{7-13}$ aralkyl optionally interrupted with one or more heteroatom; n is an integer from 0 to 2; and m is an integer from 0 to 3. These compounds act as antagonists at the ionotropic NMDA (N-methyl-(D)-aspartic acid) receptor.

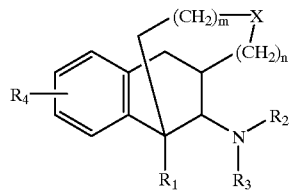

formula I

19 Claims, 3 Drawing Sheets

OTHER PUBLICATIONS

P.J. Fray, B.J. Sahakian, T.W. Robbins, G.F. Koob & S.D. Iversen, "Psychopharmacology" 69, An Observational Method for Quantifying the Behavioural Effects of Dopamine Agonists: Contrasting Effects of d–Amphetamine and Apomorphine, 1980, pp. 253–259.

N.W. Dunham & T.S. Miya; "Journal of the American Pharmaceutical Association" XLVI(3), A Note on a Simple Apparatus for Detecting Neurological Deficit in Rats and Mice, 1957, pp. 208–209.

J. Hughes, H.W. Kosterlitz & F.M. Leslie, "Brit J. Pharmac." 53, Effect of Morphine on Adrenergic Transmission in the Mouse Vas Deferens. Assessment of Agonist and Antagonist Potencies of Narcotic Analgesics, 1975, pp. 371–381.

J.W. Olney, Patterns Clin. Expression Genet. Var., Toxic Effects of Glutamate and Related Amino Acids on the Developing Central Nervous System, 1974, pp. 501–512.

R.L. Follenfant, G.W. Hardy, L.A. Lowe, C. Schneider & T.W. Smith, "Brit. J. Pharmacol.", 93, Antinociceptive effects of the novel opioid peptide BW443C compared with classical opiates; peripheral versus central actions, 1988, pp. 85–92.

F.M. Leslie, "Pharmacological Reviews", 39(3), Methods Used for the Study of Opioid Receptors, 1987 pp. 197–249.

C.J. Fowler & G.L. Fraser, "Neurochem. Int." 24(5), Opioid Receptors and Their Subtypes, A Critical Review with Emphasis on Radioligand Binding Experiments, 1994, pp. 401–427.

R.B. Raffa, A. Kim, K.C. Rice, B.R. De Costa, E.E. Codd & R.B. Rothman, "Peptides" 15(3), Low Affinity of FMRFamide and Four FaRPs (FMRFamide–Related Peptides), Including the Mammalian–Derived FaRPs F–8–Famide (NPFF) and A–18–Famide, for Opioid Receptors, 1994, pp. 401–404.

R.B. Rothman, V. Bykov, B.R. De Costa, A.E. Jacobson, K.C. Rice & L.S. Brady, "Peptides" 11, Interaction of Endogenous Opioid Peptides and Other Drugs With Four Kappa Opioid Binding Sites in Guinea Pig Brain, 1990, pp. 311–331.

J.A.H. Lord, A.A. Waterfield, J. Hughes & H.W. Kosterlitz, "Nature" 267(9), Endogenous opioid peptides: multiple agonists and receptors, 06–1977, pp. 495–499.

E. Siegmund, R. Cadmus and G. Lu, "P.S.E.B.M." 95, A Method for Evaluating both Non–Narcotic and Narcotic Analgesics (23345), 1957, pp. 729–731.

W.R. Martin, C.G. Eades, J.A. Thompson, R.E. Huppler and P.E. Gilbert, "Journal of Pharmacology and Experimental Therapeutics" 197(3), The Effects of Morphine and Nalorphine–Like Drugs in the Nondependent and Morphine–Dependent Chronic Spinal Dog, 1976, pp. 517–533.

POLYCYCLIC ALCALOID-DERIVATIVES AS NMDA-RECEPTOR ANTAGONISTS

FIELD OF THE INVENTION

The invention relates to novel polycyclic alkaloids which can bind or antagonize the NMDA (N-methyl-(D)-aspartic acid) receptor complex or otherwise protect neurons against excitatory amino acid receptor-induced degeneration. In another aspect, the invention relates to a method of inhibiting NMDA receptor activation in a mammal using the novel polycyclic alkaloids of the invention.

BACKGROUND OF THE INVENTION

Excitatory amino acids such as L-glutamate (Glu) and L-aspartate (Asp), are major neurotransmitters in the mammalian central nervous system. Multiple acidic amino acid receptor subtypes exist for these acid amino acid neurotransmitters. For example, these include ion channel-linked receptors mediating neuronal depolarization, named after the protypical agonists N-methyl-D-aspartate (NMDA), alpha-amino-5-methyl-4-isoxazolepropionic acid (AMPA), kainate and a putative presynaptic stimulator, L-2-amino-4-phosphonobutyrate (L-AP4). A fifth excitatory amino acid receptor is the metabotropic receptor, linked to phosphoinositide metabolism (Farooqui and Horrocks, Brain Res. Rev. 16, 171, 1991).

NMDA receptors play a specialized role due to the unique properties of their linked ion channels and participate in various plastic neuronal events including initiation of long-term potentiation, which is a proposed substrate of learning and memory and the establishing of synaptic contacts during neuronal development. NMDA receptors are also involved in other processes such as the transmission of sensory information (MacDermott and Dale, Trends Neurosci. 10, 280, 1987).

Apart from their important physiological roles, excitatory acidic amino acids such as NMDA are also involved in pathophysiological events in the central nervous system. Abnormally low levels of glutamic acid (Glu) can compromise normal levels of excitation and cause, for example, learning and memory deficits. Excessive levels of Glu can produce toxic effects. The term "excitotoxicity" was coined by Olney (in Hyhan W. L. [ed]: "Heritage Disorders of Amino Acids Metabolism" New York: Macmillan pp. 501–512, 1989) to describe the process by which excitatory amino acids can cause neuronal cell death.

Evidence indicates that NMDA receptors exist in the peripheral tissues and that activation of these receptors may be involved in a mechanism of lung and other organ injury (Said, S. I. et al., Letters to Neuroscience, 65, 943–946, 1995). This cytotoxic process is mainly mediated by an over-stimulation of NMDA receptors and may occur in cases of cerebral stroke, cerebral ischaemia, epilepsy, Alzheimer's disease, AIDS-related dementias, traumatic brain injury and other neurodegenerative disorders (Olney, Ann. Rev. Pharmacol. Toxicol. 30: 47–71, 1990; Foster et al, in "Current and future Trends in Anticonvulsant, Anxiety and Stroke Therapy" Wiley-Liss, Inc. pp. 301–329, 1990; Rogawski and Porter, Pharmacol. Rev., 42: 223–286, 1990).

The NMDA receptor comprises several binding domains that interact with each other for proper functioning and modulation of nerve cell activity. It is theorized that the NMDA receptor forms a complex acting as a receptor-linked ion channel. Essentially, the function of the receptor is to bind NMDA or the natural amino acids, Glu or Asp, and open an associated ion channel that allows the entry of sodium ($Na^+$) and calcium ($Ca^{2+}$) into the stimulated neuron as well as the exit of potassium ($K^+$).

Whereas the ion channels of other excitatory amino acid receptors (AMPA, kainate and L-AP4) are only permeable to $Na^+$ and $K^+$, the NMDA receptor channel is also permeable to $Ca^{2+}$. This feature may be of importance for the proposed role of this receptor in both short and long-term plasticity such as learning, memory and neuropathology.

Intracellular $Ca^{2+}$ is responsible for the regulation of a large variety of cellular activities (Farooqui and Horrocks, Brain Res. Rev. 16, 171; 1991). An overstimulation of brain NMDA receptors, observed in cases of anoxia, ischaemia and hypoglycemia, results in a build-up of the concentration of Ca++ in stimulated neurons and a cascade of intracellular events (activation of phospholipases [$PLA_2$, PLC], lipases, proteases and endonucleases) that lead to neuronal cell death (Farooqui and Horrocks, Brain Res. Rev. 16, 171; 1991).

There is therefore a need for compounds which can bind or antagonize the NMDA receptor complex or otherwise protect neurons against excitatory amino acid receptor-induced degeneration.

SUMMARY OF THE INVENTION

The present invention relates to novel polycyclic alkaloids that act as antagonists at the ionotropic NMDA (N-methyl-(D)-aspartic acid) receptor having the general structure represented by formula I:

formula I wherein
$R_1$ is H, $C_{1-6}$ alkyl, or $C_{6-12}$ aryl optionally substituted with polar groups;

$R_2$ and $R_3$ are independently H, OH, $C_{1-6}$ alkyl, —C(NH)—$NH_2$, a positively charged group, or $C_{7-13}$ aralkyl optionally substituted with $NH_2$, OH, $C_{1-6}$ alkyl, or halogen; or $R_2$ and $R_3$ together form a 5 to 6 member ring optionally incorporating a heteroatom;

$R_4$ is H, $C_{1-6}$ alkyl, $OR_6$, $SR_6$ or $N(R_6)_2$, wherein each $R_6$ is independently H or $C_{1-3}$ alkyl;

X is O, S, SO, $SO_2$, N—$R_5$, or C—$(R_5)_2$, wherein each $R_5$ is independently H, $C_{1-6}$ alkyl, or $C_{7-13}$ aralkyl optionally interrupted with one or more heteroatom;

n is an integer from 0 to 2;

m is an integer from 0 to 3;

with the proviso that when X is $CH_2$ then $R_1$ is not $CH_3$, $R_2$ and $R_3$ are not both H, $R_4$ is not OH, m is not 3 and n is not 0.

It will be appreciated by those skilled in the art that the compounds of formula (I), depending of the substituents, may contain one or more chiral centers and thus exist in the form of many different isomers, optical isomers (i.e. enantiomers) and mixtures thereof including racemic mixtures. All such isomers, enantiomers and mixtures thereof including racemic mixtures are included within the scope of the invention.

In another aspect of the present invention there is provided a method of inhibiting NMDA receptor activation in a mammal comprising administering to said mammal an NMDA receptor antagonizing amount of a compound according to claim 1.

In another aspect, there is provided a method of treating or preventing cell damage or cytotoxicity mediated by NMDA receptor activation in a mammal comprising administering to said mammal a pharmaceutically effective amount of a compound according to claim 1.

In a further aspect of the invention, there are provided methods of treating or preventing neuro degenerative disease, stroke, epileptic seizures and convulsions in a mammal comprising administering to said mammal a pharmaceutically effective amount of a compound according to claim 1.

DETAILED DESCRIPTION OF THE INVENTION

The present invention relates to novel polycyclic alkaloids according to formula I:

formula I wherein $R_1$–$R_4$, X, m and n are as previously defined.

The following common abbreviations are used throughout the specification:

'EAA' refers to excitatory amino acid.
'NMDA' refers to N-methyl-(D)-aspartic acid.
'AMPA' refers to alpha-amino-5-methyl-4-isoxazolepropionic acid.

The term $CD_{50}$ as shown in Table 1 is defined as the dose of drug which induces a 50% reduction in the number of deaths caused by NMDA administration.

As used in this application, the term 'alkyl' represents a saturated or unsaturated, substituted (by one or more halogen, hydroxyl, amino, or $C_{6-20}$ aryl group) or unsubstituted; straight chain, branched chain, or cyclic hydrocarbon moiety wherein said straight chain, branched chain, or cyclic hydrocarbon moiety can be interrupted by one or more heteroatoms (such as oxygen, nitrogen or sulfur).

The term 'aryl' represents a carbocyclic moiety which is optionally substituted (e.g. one or more $C_{1-6}$ alkyl, halogen, hydroxyl, amino), interrupted by one or more heteroatoms (e.g., N, O or S) and containing at least one benzenoid-type ring (e.g. phenyl and napthyl).

The term 'aralkyl' represents an aryl group attached to the adjacent atom by an alkyl (e.g. benzyl).

The compounds of the present invention are represented by formula (I) as defined above.

Preferably, $R_1$ is cyclohexyl.
Preferably, $R_1$ is phenyl optionally substituted with polar groups.
Preferred polar groups are COOH, $NH_2$ or guanidino.
More preferably, $R_1$ is H.
Most preferably, $R_1$ is $CH_3$.
Preferably, $R_2$ —C(NH)—$NH_2$.
Preferably, $R_2$ is a positively charged amino group.
More preferably, $R_2$ is H.
Preferably $R_3$ is $C_{1-6}$ alkyl.
More preferably, $R_3$ is $OCH_3$.
Most preferably, $R_3$ is H.
Most preferably, $R_3$ is OH.
Preferably $R_4$ is $OC_{1-6}$ alkyl
Preferably $R_4$ is halogen.
More preferably, $R_4$ is OH.
Most preferably, $R_4$ is $OCH_3$.
Preferably, X is SO.
Preferably, X is $SO_2$.
Preferably, X is $NR_5$.
More preferably, X is O.
Most preferably, X is S.
Preferably $R_5$ $C_{1-6}$ alkyl.
More preferably, $R_5$ is $CH_3$.
Most preferably, $R_5$ is H.
Preferably n is 0.
Preferably, m is 3.

A preferred compound of the invention includes:
compound #8a: 5,6,7,8,9,11,12-heptahydro-3-methoxy-5-methyl-10-thia-5,11-methanobenzocyclodecen-13-β-hydroxylamine;

A preferred compound of the invention includes:
compound #8b: 5,6,7,8,9,11,12-heptahydro-3-methoxy-5-methyl-10-thia-5,11-methanobenocyclodecen-13-amine;

A preferred compound of the invention includes:
compound #9: 5,6,7,8,9,11,12-heptahydro-3-hydroxy-5-methyl-10-thia-5,11-methanobenzocyclodecen-13-amine (sulphazocine);

A preferred compound of the invention includes:
compound #9a (−)-trans-5,6,7,8,9,11,12-heptahydro-10-thia-3-hydroxy-5-methyl-5,11-methanobenzocyclodecen-13-amine;

A preferred compound of the invention includes:
compound #9b (+)-trans-5,6,7,8,9,11,12-heptahydro-10-thia-3-hydroxy-5-methyl-5,11-methanobenzocyclodecen-13 amine;

A preferred compound of the invention includes:
compound #10: 5,6,7,8,9,11,12-heptahydro-3-hydroxy-5-methyl-10-thia-5,11-methanobenzocyclodecene-13-β-hydroxylamine;

A preferred compound of the invention includes:
compound #11 trans-5,6,7,8,9,11,12-heptahydro-10-thia-3-hydroxy-5-methyl-5,11-methanobenzocyclodecen-13-guanidine.

A preferred compound of the invention includes:
compound #12 trans-5,6,7,8,9,11,12-heptahydro-10-sulphono-3-hydroxy-5-methyl-5,11-methanobenzocyclodecen-13-amine;

A preferred compound of the invention includes:
compound #13: 5,6,7,8,9,11,12-heptahydro-3-hydroxy-5-methyl-5, 11-methanobenzocyclodecene-13-amine.

A more preferred compound of the invention is:
compound #11: trans-5,6,7,8,9,11,12-heptahydro-10-thia-3-hydroxy-5-methyl-5,11-methanobenzocyclodecen-13-guanidine.

A most preferred compound of the invention is:

compound #9: 5,6,7,8,9,11,12-heptahydro-3-hydroxy-5-methyl-10-thia-5,11 methanobenzocyclodecen-13-amine (sulphazocine)

A most preferred compound of the invention is:

synthesis as well as the resulting NMDA receptor antagonist compounds of the present invention follow. Successful preparation of these compounds is possible by way of several synthetic routes one of which is outlined in Scheme 1.

SCHEME 1 compound #10: 5,6,7,8,9,11,12-heptahydro-3-hydroxy-5-methyl-10-thia-5,11-methanobenzocyclodecene-13-β-hydroxylamine;

A most preferred compound of the invention is:

compound #11 trans-5,6,7,8,9,11,12-heptahydro-10-thia-3-hydroxy-5-methyl-5,11-methanobenzocyclodecen-13-guanidine.

The compounds of the present invention can be synthesized using conventional preparative steps and recovery methods known to those skilled in the art of organic and bio-organic synthesis, while providing a new and unique combinations for the overall synthesis of each compound. Preferred synthetic routes for intermediates involved in the The steps illustrated in Scheme 1 can be briefly described as follows:

Step 1:
Compound I, an alkyl-1-tetralone, is treated with an appropriate Grignard Reagent such as methyl magnesium bromide in a dry non-polar solvent such as THF, to generate the tertiary alcohol, Compound II.

Step 2:
The alcohol, Compound II is dehydrated under acidic conditions, such as aqueous saturated $NH_4Cl$, to yield Compound III.

Step 3:
The double bond at position 1 on the olefin is epoxidized using standard reagents and solvents, such monoperoxyphthalic acid magnesium salt in isopropanol, to produce the epoxide, Compound IV.

Step 4:

The epoxide is rearranged under acidic conditions, such as aqueous $NaHCO_3$, using standard techniques to generate the ketone, Compound V.

Step 5:

Alkylation of the bis-alkyl-2-tetrone (Compound V) is accomplished under basic conditions in non-polar solvent using a dihaloalkyl reagent, such as dibromobutane, to yield Compound VI.

Step 6:

Nucleophilic displacement of bromide is accomplished with an appropriate reagent, such as potassium thiacetate to produce Compound VII.

Step 7:

The 3 position of the S-acylated tetralone (Compound VII) is halogenated in a non-polar solvent, such as a mixture of benzene and dry THF, using an appropriate reagent and non-polar solvent such as Bromine in dry THF to generate Compound VIII.

Step 8:

Cyclization is affected under basic conditions using standard reagents and solvents such as lithium bromide and dry THF under Argon, with the addition of a base such as sodium methoxide, generating the polycyclic compound (Compound IX).

Step 9:

The ketone group of compound IX is converted to an alkyloxime using standard procedures well known in the art affording compound X.

Steps 10 and 11:

Compound X is reduced using a Borane-THF complex. If conducted in THF, a 50:50 mixture of compounds XI and XII is obtained. If the reaction is conducted in diglyme (2-methoxyethyl ether), the amine, (Compound XII) is selectively produced.

Step 12:

Compound XI can be recycled and reduced to the amine using a Borane-THF complex conducted in diglyme to yield Compound XII.

Compounds of the present invention bind to and block activation of the ionotropic NMDA receptor and thereby prevent excessive $Ca^{+2}$ entry into neurons in NMDA-receptor mediated events that are typical of hypoxic and/or ischemic conditions. Excessive entry of calcium into neuronal cells is a prelude to neuronal damage that follows head injury, strokes, and epileptic seizures; is associated with degenerative diseases such as Alzheimer's disease, Huntington's disease, Parkinson's disease and amytrophic lateral sclerosis (ALS); and peripheral neurotoxicity involved in lung and other organ injury.

Accordingly the present invention further relates to the use of compounds according to formula (I) for inhibiting NMDA receptor activation as well as for treating and preventing cell damage or cytotoxicity mediated by NMDA receptor activation in a mammal.

The present invention provides compounds that block EAA-induced convulsions in an in vivo rodent model. It has been found that compounds of the present invention block mortality induced by NMDA, AMPA or bicuculline.

It is appreciated that the compounds of the present invention can be modified by one skilled in the art in such a manner as to attach labels such as radioactive labels enabling detection of the compound for use as a radiotracer. The compounds of the present invention may be used as NMDA antagonists in vitro or ex vivo as in the case of radio-labeling agents, radiotracers for use with Positron Emission Tomography, paramagnetic agents for use in Magnetic Resonance Imaging, and NMDA receptor-linked calcium channel antagonists.

It is appreciated that the compounds of the present invention can be modified by one skilled in the art in such a manner as to prevent access into the central nervous system such that they can function as NMDA receptor antagonists in peripheral tissues to protect against and/or minimize cytotoxicity (neurotoxicity) involved in peripheral NMDA receptor mediated events.

The present invention also provides pharmaceutical compositions which comprise a pharmaceutically effective amount of the compounds of this invention, or pharmaceutically acceptable salts thereof, and, optionally a pharmaceutically acceptable carrier or adjuvant. The term "pharmaceutically effective amount" refers to the required amount of compound to be administered to a mammal in order to reduce or inhibit NMDA receptor activation, cell damage, convulsions or symptoms associated with neuro degenerative diseases. The amount will depend on factors such as the particular indication being treated, mode of administration, size of individual being treated etc.

Therapeutic methods of this invention comprise the step of treating patients in a pharmaceutically acceptable manner with those compounds or compositions. Such compositions may be in the form of tablets, capsules, caplets, powders, granules, lozenges, suppositories, reconstitutable powders, or liquid preparations, such as oral or sterile parenteral solutions or suspensions.

The therapeutic agents of the present invention may be administered alone or in combination with pharmaceutically acceptable carriers. The proportion of each carrier is determined by the solubility and chemical nature of the compound, the route of administration, and standard pharmaceutical practice.

In order to obtain consistency of administration, it is preferred that a composition of the invention is in the form of a unit dose. The unit dose presentation forms for oral administration may be tablets and capsules and may contain conventional excipients. For example, binding agents, such as acacia, gelatin, sorbitol, or polyvinylpyrolidone; fillers, such as lactose, sugar, maize-starch, calcium phosphate, sorbitol or glycine; tabletting lubricants such as magnesium stearate; disintegrants, such as starch, polyvinylpyrrolidone, sodium starch glycollate or microcrystalline cellulose; or pharmaceutically acceptable wetting agents such as sodium lauryl sulphate.

The compounds may be administered parenterally; this being intramuscularly, intravenously, or subcutaneously. For parenteral administration, the compounds may be used in the form of sterile solutions containing other solutes, for example, sufficient saline or glucose to make the solution isotonic.

The compounds may be administered orally in the form of tablets, capsules, or granules containing suitable excipients such as starch, lactose, white sugar and the like. The compounds may be administered orally in the form of solutions which may contain coloring and/or flavoring agents. The compounds may also be administered sublingually in the form of tracheas or lozenges in which each active ingredient is mixed with sugar or corn syrups, flavoring agents and dyes, and then dehydrated sufficiently to make the mixture suitable for pressing into solid form.

The solid oral compositions may be prepared by conventional methods of blending, filling, tabletting, or the like. Repeated blending operations may be used to distribute the active agent throughout those compositions employing large quantities of fillers. Such operations are, of course, conventional in the art. The tablets may be coated according to methods well known in normal pharmaceutical practice, in particular with an enteric coating.

Oral liquid preparations may be in the form of emulsions, syrups, or elixirs, or may be presented as a dry product for reconstitution with water or other suitable vehicle before use. Such liquid preparations may or may not contain conventional additives. For example suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acacia; non-aqueous vehicles (which may include edible oils), such as almond oil, fractionated coconut oil, oily esters selected from the group consisting of glycerine, propylene glycol, ethylene glycol, and ethyl alcohol; preservatives, for instance metyl parahydroxybenzoate, ethyl parahydroxybenzoate, n-propyl parahydroxybenzoate, or n-butyl parahydroxybenzoate of sorbic acid; and, if desired, conventional flavoring or coloring agents.

For parenteral administration, fluid unit dosage forms may be prepared by utilizing the compound and a sterile vehicle, and, depending on the concentration employed, may be either suspended or dissolved in the vehicle. Once in solution, the compound may be injected and filter sterilized before filling a suitable vial or ampoule and subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying the composition). Parenteral suspensions may be prepared in substantially the same manner, except that the compound should be suspended in the vehicle rather than being dissolved, and, further, sterilization is not achievable by filtration. The compound may be sterilized, however, by exposing it to ethylene oxide before suspending it in the sterile vehicle. A surfactant or wetting solution may be advantageously included in the composition to facilitate uniform distribution of the compound.

The pharmaceutical compositions of this invention comprise a pharmaceutically effective amount of a compound of this invention and a pharmaceutically acceptable carrier. Typically, they contain from about 0.1% to about 99% by weight, preferably from about 10% to about 60% by weight, of a compound of this invention, depending on which method of administration is employed.

The present invention also provides a method for treatment of NMDA receptor mediated cytotoxicity and/or disease in patients, such as mammals, including humans, which comprises the step of administering to the patient a pharmaceutically effective amount of a compound, a pharmaceutically acceptable salt thereof, or a pharmaceutical composition as described above.

Physicians will determine the dosage of the present therapeutic agents which will be most suitable. Dosages may vary with the mode of administration and the particular compound chosen. In addition, the dosage may vary with the particular patient under treatment. The dosage of the compound used in the treatment will vary, depending on the seriousness of the disorder, the weight of the patient, the relative efficacy of the compound and the judgment of the treating physician. Such therapy may extend for several weeks, in an intermittent or uninterrupted manner, until the patient's symptoms are eliminated.

To further assist in understanding the present invention, the following non-limiting examples are provided.

EXAMPLE 1

Preparation of 1,2-dihydro-7-methoxy-4-methylnapthalene 7-methoxy-1-tetralone (25 g) was dried via azeotropic distillation of toluene and dissolved in dried THF (200 ml). The solution was cooled to −70° C. (under Ar and methyl magnesium bromide (1.4 M in toluene/THF, 187.5 ml) was added. The combined reaction mixture was allowed to stir at ambient temperature overnight. It was carefully treated with aqueous saturated $NH_4Cl$ and extracted with ethylacetate. The latter solution was washed with brine, dried over $MgSO_4$ and evaporated. The residue was dissolved in benzene (150 ml), p-TSOH (0.1 g) was added and the mixture was heated to reflux using a Dean-Stark condenser until the dehydration reaction was complete. This benzene solution was diluted with ethylacetate, washed with $NaHCO_3$, dried over $MgSO_4$ and evaporated. The residue was extracted with hexanes, passed through a silica gel column and eluted with a mixture of hexanes and ethylacetate (1:0, 400:1, 200:1). The yield of the product was 20.87 g (84.42%).

$^1$H NMR (300 MHz, $CDCl_3$) δ: 2.05 (s, 3H); 2.23 (m, 2H); 2.69 (t, 2H); 3.81 (s, 3H) 5.88 (m, 1H); 6.68–7.06 (m, 3H) ppm.

EXAMPLE 2

Preparation of 7-methoxy-1-methyl-2-tetralone

-continued

Dihydro-7-methoxy-4-methylnapthalene (20.87 g) was dissolved in isopropanol (100 ml) and cooled in an ice bath. Monoperoxyphthalic acid magnesium salt (mmpp) (17 g) was added, then water (50 ml) was added and the mixture was stirred at room temperature for 2 hours. When oxidation was complete, the product mixture was hydrolyzed with aqueous $NaHCO_3$, partially evaporated and extracted with ethylacetate. The latter extract was washed with brine and evaporated. The residue was dissolved in a mixture of ethanol (156 ml), water (121 ml) and conc. $H_2SO_4$ (24.3 ml), and heated to reflux under $N_2$ atmosphere for 3 hours, cooled and neutralized with $NaHCO_3$. After partial evaporation, the residue was extracted with ethylacetate, washed with brine, dried over $MgSO_4$ and evaporated. The product was purified on a silica gel column using a mixture of hexanes and ethylacetate (100:1, 50:1, 50:1.5). The yield of the product was 16.2 g (71%).

$^1$H NMR (300 MHz, $CDCl_3$) δ: 1.47 (d, 3H); 2.55 (m, 2H); 3.02 (m, 2H); 3.5 (m, 1H); 3.81 (s, 3H); 6.75–6.77 (m, 3H) ppm. IR (film) 1714 $cm^{-1}$

EXAMPLE 3

Preparation of 1-(4'-bromobutyl)-1-methyl-7-methoxy-2-tetralone

7-Methoxy-1-methyl-2-tetralone (4 g) was dried via azeotropic distillation of toluene, dissolved in dry THF (150 ml), cooled in an ice bath under Ar atmosphere and sodium bis(trimethylsilyl) amide solution (NaHMDS)(1 M in THF, 23.13 ml) was added and stirred for ½ hour. 1,4-Dibromobutane (9.78 ml) was added and the reaction mixture was allowed to warm up to room temperature overnight, after which it was hydrolyzed with brine, extracted with ethylacetate, dried over $MgSO_4$ and evaporated. The product mixture was purified on a silica gel column using a mixture of hexanes and ethylacetate (200:1, 150:1,100:1, 75:1 and 50:1). The yield of the product was 5.19 g (76%).

$^1$H NMR: (300 MHz, $CDCl_3$) δ: 1.09 (m, 2H); 1.37 (s, 3H); 1.71 (m, 3H); 2.1 (m, 3H); 2.68 (m, 2H); 2.97 (m, 2H); 3.26 (t, 2H); 3.8 (s, 3H), 6.72–7.09 (m, 3H) ppm.

EXAMPLE 4

Preparation of 1-(4'-acetothiobutyl)-1-methyl-7-methoxy-2-tetralone 1-(4'-Bromobutyl)-1-methyl-7-methoxy-2-tetralone (4.48 g) was dried via azeotropic distillation of toluene and dissolved in dry DMF (25 ml). Potassium thioacetate (5.86 g) was added and the mixture was allowed to stir under Ar atmosphere overnight, after which it was extracted with ethylacetate, washed with brine, dried over $MgSO_4$ and evaporated. The residue was purified on a silica gel column using a mixture of hexanes and ethylacetate (75:1, 50:1, 20:1). The yield of the product was 3.9 g (88.3%).

$^1$H NMR (300 MHz, $CDCl_3$) δ: 0.99 (m, 2H) ; 1.5 (m, 6H); 2.07 (m, 1H); 2.25 (s, 3H); 2.65 (m, 4H); 2.95 (m, 2H); 3.79 (s, 3H); 6.71–7.08 (m, 3H) ppm.

EXAMPLE 5

Preparation of an Epimeric Mixture of 3-bromo-1-(4'-acetothiobutyl)-1-methyl-7-methoxy-2-tetralone 1-(4'-Acetothiobutyl)-1-methyl-7-methoxy-2-tetralone (4 g) was dried via azeotropic distillation of toluene. It was dissolved in a mixture of benzene (244 ml) and dry THF (64 ml) and stirred at room temperature under Ar atmosphere. Bromine (0.8 ml) was dissolved in dry THF (26 ml) and gradually added to the reaction mixture under Ar flow. After 1 hour of stirring, the product mixture was hydrolyzed with aqueous $NaHCO_3$, extracted with ethylacetate, washed with brine, dried over $MgSO_4$ and evaporated. The residue was dried via azeotropic distillation of toluene and then dried further under high vacuum.

EXAMPLE 6

Preparation of 5,6,7,8,9,11,12-heptahydro-3-methoxy-5-methyl-10-thia-5,11-ethanobenzocyclodecen-13-one An epimeric mixture of 3-bromo-1-(4'-acetothiobutyl)-1-methyl-7-methoxy-2-tetralone (approximately 6.25 mmol) was dried via azeotropic distillation of toluene and dissolved in dry THF (200 ml), Lithium Bromide (dry, 0.54 g) was added, the solution was degassed with Ar at room temperature for one hour, and was cooled in an ice bath, well stirred, with a gentle flow of Ar passing through it. Sodium methoxide (0.5 M in Methanol, 13.75 ml) was dissolved in dry THF (75 ml), degassed with Ar at room temperature for one hour, after which it was added to the latter solution through a syringe pump over 4 hours. The combined reaction mixture was stirred for an additional ½ hour, diluted with ethylacetate (100 ml), washed with brine, dried over $MgSO_4$ and evaporated. The residue was purified on a silica gel column using a mixture of hexanes and ethylacetate (75:1, 50:1). The yield of product was approximately 50–55%. It solidified on standing.

$^1$H NMR (300 MHz, $CDCl_3$) δ: 1.4–1.95 (m, 4H); 2.85 (m, 2H); 2.7–3 (m, 2H); 3.4 (m, 1H); 3.82 (m, 4H); 6.7–7.1 (m, 3H) ppm. IR (film) 1693, 1609 cm$^{-1}$

EXAMPLE 7

Preparation of Epimeric 5,6,7,8,9,11,12 hepta hydro-3-methoxy-5-methyl-10-thia-5,11-methanobenzocyclodecen-13-oxime 5,6,7,8,9,11,12-Heptahydro-3-methoxy-5-methyl-10-thia-5,11-methanobenzocyclodecen-13-one (1.32 g) was dried via azeotropic distillation of toluene, mixed with hydroxyl amine hydrochloride (2.64 g) and dry pyridine (5.2 ml) was added. Combined mixture was heated to 80° C. for 2 days. It was cooled, diluted with $CH_2Cl_2$ and washed with brine. After drying over $MgSO_4$, the solvent was evaporated off and the residue was purified on a silica gel column using a mixture of hexanes and ethylacetate (50:1, 25:1, 10:1, 5:1 8 2:1). The yield of the product was 1.22 g. (92%).

$^1$H NMR (300 MHz, $CDCl_3$) δ; 1.2–1.9 (m, 9H); 2.4 (m, 2H); 2.85 (m, 2H); 3.2 (dd, 1H); 3.8 (s, 3H); 5.11 (t, 1H); 6.6–7.1 (m, 3H) ppm. IR (film) 1609, 2200, 3250 cm$^{-1}$ Mass Spectrometry: m/z 292.

EXAMPLE 8

Preparation of 5,6,7,8,9,11,12-heptahydro-3-methoxy-5-methyl-10-thia-5,11-methanobenzocyclodecen-13-hydroxylamine Compound #8a and 5,6,7,8,9,11,12-heptahydro-3-methoxy-5-methyl-10-thia-5,11-methanobenzocyclodecen-13-amine Compound #8b compound #8a compound #8b 5,6,7,8,9,11,12-Heptahydro-3-methoxy-5-methyl-10-thia-5,11-methanobenzocyclodecen-13-oxime (isomeric mixture, 0.3 g) was dried with toluene and dissolved in dry THF (30 ml). It was cooled in an ice bath under Ar atmosphere. Borane-THF complex (1M solution in THF, 7.87 ml) was added and the combined mixture was heated to reflux for 30 hours. It was cooled in an ice bath. Water (0.4 ml) and concentrated HCl (0.6 ml) were added carefully in respective order. The mixture was heated to reflux for 15 minutes, cooled and evaporated. The residue was basified with concentrated $NH_4OH$ to pH 12, extracted with $CH_2Cl_2$, washed with brine, dried over $MgSO_4$ and evaporated. The residue was purified on a silica gel column using a mixture of hexanes and ethylacetate (50:1, 20:1, 10:1, 5:1, 5:1.5, 2:1, 1:1 and 1:2). The yield of 5,6,7,8,9,11,12-heptahydro-3-methoxy-5-methyl-10-thia-5,11-methanobenzocyclodecen-13-hydroxylamine was 0.073 g (23.1%). It was crystallized from a mixture of ethylacetate and hexanes.

$^1$H NMR (300 MHz, $CDCl_3$) δ: 1.1–1.91 (m, 9H); 2.3 (m, 2H); 3.30 (d, 1H); 3.37 (m, 2H); 3.7 (m, 1H), 3.78 (s, 3H), 6.6.–7.1 (m, 3H) ppm. IR (film): 1612, 3300 cm$^{-1}$ Mass Spectrometry: 293.8, 275.8, 260.8.

The structure of #8a was confirmed by single crystal X-ray crystallography.

The yield of 5,6,7,8,9,11,12-heptahydro-3-methoxy-5-methyl-10-thia-5,11-methanobenzocyclodecen-13-amine was 0.0968 g. (32%). The free base was soluble in hexanes.

$^1$H NMR (300 MHz, CDCl$_3$) δ: 0.8–2.5 (m, 11H), 3.18 (m, 3H), 3.6 (q, 1H), 3.8 (s, 3H) 6.6–7.1 (m, 3H) ppm.

This product was dissolved in ether (40 ml) and acidified with Methanol-HCl. The suspension was allowed to settle and filtered. The precipitate was washed with ether and dried, yielding 0.090 g of product.

$^1$H NMR (300 MHz, CDCl3) δ: 0.8–1.7 (m, 6H); 1.8 (m, 2H); 2.0–2.5 (m, 3H); 3.45 (m, 2H); 3.5 (m, 2H); 3.8 (S, 3H) 6.7–7.1 (m, 3H) ppm. Mass Spectrometry: m/z 278.

EXAMPLE 9

Preparation of 5,6,7,8,9,11,12-heptahydro-3-hydroxy-5-methyl-10-thia-5,11 methanobenzocyclodecen-13-amine (sulphazocine) Compound #9 compound #9

5,6,7,8,9,11,12-Heptahydro-3-methoxy-5-methyl-10-thia-5,11-methanobenzocyclodecen-13-amine (0.260 g) was dried via azeotropic distillation of toluene and dissolved in dry CH$_2$Cl$_2$ (40 ml). It was cooled to −70° under Ar atmosphere. Boron tribromide solution (1M solution in CH$_2$Cl$_2$, 187 ml) was added and the combined mixture was allowed to stir at ambient temperature overnight. The reaction mixture was hydrolyzed with NaHCO$_3$, the pH lowered with NH$_4$OH to 12, and extracted with CH$_2$Cl$_2$. The latter solution was dried over MgSO$_4$ and evaporated. The residue was purified on a silica gel column using a mixture of toluene and ethylacetate. (10:1, 5:1, 2:1, 1:1, 1:2).

The yield of 5,6,7,8,9,11,12-heptahydro-3-hydroxy-5-methyl-10-thia-5,11-methanobenzocyclodecen-13-amine was 0.162 g (65%).

$^1$H NMR (350 MHz, DMSO-D$_6$) δ: 1.02 (m, 1H); 1.25 (m, 5H); 1.55 (m 2H); 2.01 (m, 2H); 2.55 (m, 1H); 2.97 (d, 1H) 3.08 (m, 1H), 3.14 (m, 2H); 6.4–6.9 (m, 3H) ppm.

The above product was converted to its hydrochloride salt and purified via HPLC.

EXAMPLE 10

Preparation of 5,6,7,8,9,11,12-hepta hydro-3-hydroxy-5-methyl-10-thia-5,11-methanobenzocyclodecen-13-hydroxylamine Compound #10 compound #10

5,6,7,8,9,11,12-heptahydro-3-methoxy-5-methy-10-thia-5,11-methanobenzoxycyclodecen-13-hydroxyl amine (0.166 g) was dissolved in a mixture of acetic acid (4.5 ml) and 48% HBr (4.5 ml). It was cooled, neutralized carefully with NaHCO$_3$ and extracted with CH$_2$Cl$_2$. Latter solution was washed with brine, dried over MgSO$_4$ and evaporated. Residue was purified on a silica gel column using a mixture of hexanes and ethylacetate (10:1, 10:1.5, 5:1). The yield of 5,6,7,8,9,11,12-heptahydro-3-hydroxy-5-methyl-10-thia-5, 11-methanobenzocyclodecen-13-hydroxylamine was 0.035 g (22%).

$^1$H NMR (300 MHz, CDCl$_3$) δ: 1.1–1.91 (m, 9H); 2.30 (m, 2H); 3.28 (m, 1H), 3.34 (m, 2H); 3.7 (m, 1H), 6.6–7.0 (m, 3H) ppm.

Above product was converted to its hydrochloride salt and purified by HPLC.

EXAMPLE 11

5,6,7,8,9,11,12-heptahydro-5-methyl-5,11-methanobenzocyclodecene-13-amine -•-HCl- Compound #13

Compound #13 was obtained from Astra, Sweden(CAS 53648-55-8) (J. W. Downing, Brit J. Anaesth., 1981, 53, 59; see also Freed, M. E., et al., J. Med. Chem., 16:595–599, 1973).

EXAMPLE 12

Preparation of Compound #9a (−)-trans-5,6,7,8,9, 11,12-heptahydro-10-thia-3-hydroxy-5-methyl-5,11-methanobenzocyclodecen-13-amine Compound #9 (2.96 g) was mixed with D-tartaric acid (2.01 g) dissolved in boiling ethanol (95%, 50 mL) and filtered. The insoluble mass was washed with hot ethanol (25 mL). Combined filtrates were evaporated to dryness and the residue was redissolved in hot ethanol (20 mL). A fluffy solid mass was collected and redissolved in hot ethanol (15 mL). Crystallization was allowed to proceed undisturbed at room temperature for 2 days. Semicrystalline mass was further subjected to similar fractional crystallization process two more times. A sample at this stage was found to have a diasteromeric purity of 98% via chiral derivatization with Marfey's reagent. (0.267 g)

The tartrate salt of the title compound (0.1 g) was dissolved in hot methanol (20 mL) and transferred to a column packed with Amberlite IRA-400 (Cl⁻ form) ion exchange resin (5 g, washed successively with methanol, water, 0.1M HCl, water and methanol). The column was washed with methanol (100 mL) and water (100 mL) in succession. Combined eluents were evaporated off and lyophilized. Residue (0.076 g)

EXAMPLE 13

Preparation of Compound #9b (+)-trans-5,6,7,8,9,11,12-heptahydro-10-thia-3-hydroxy-5-methyl-5,11-methanobenzocyclodecen-13amine Compound #9-D-tartrate salt (highly enriched in dextrorotatory diastereomer 1.5 g) was mixed with $NH_4OH$ (10 mL) saturated with sodium chloride and extracted with methylene chloride. The latter was washed with brine, dried over $MgSO_4$ and evaporated. Residue (1.27 g) was mixed with L-tartaric acid (0.87 g) and boiled with ethanol (95%, 100 mL) filtered, the filtrate then being allowed to crystallize at room temperature for 2 days. The precipitated mass was allowed to crystallize slowly from hot isopropanol. A sample was found to have a diastereomeric purity of 97% via chiral derivatization with Marfey's reagent to give 0.1515 g yield.

The tartrate salt of the title compound (0.076 g) was dissolved in hot methanol (25 mL) and transferred to a column packed with activated Amberlite IRA-400 (Cl⁻ form, 5 g) which was then washed with methanol (100 mL) and water (100 mL) successively. Combined filtrates were evaporated and lyophilized. residue (0.058 g)

EXAMPLE 14
Preparation of Compound #11 trans-5,6,7,8,9,11,12-heptahydro-10-thia-3-hydroxy-5-methyl-5,11-methanobenzocyclodecen-13-guanidine Compound #9 (0.35 g) was dried via azeotropic distillation with toluene and dissolved in dry pyridine (5 mL). 1H-pyrazole-1-carboxamidine hydrochloride (1.29 g) and diisopropyl ethylamine (1.74 mL) was added. Combined mixture was heated to 80° C. under nitrogen atmosphere for 4 days. Solvent was evaporated off and the residue was purified on a silica gel column using a mixture of methylene chloride and methanol. The product (0.41 g) was dissolved in methanol saturated with hydrogen chloride (5 mL) and the solvent evaporated off. The residue was purified by HPLC yielding 0.045 g final product.

EXAMPLE 15
Preparation of Compound #12 trans-5,6,7,8,9,11,12-heptahydro-10-sulphono-3-hydroxy-5-methyl-5,11-methanobenzocyclodecen-13-amine Compound #9 (0.1 g) was dried via azeotropic distillation of toluene, dissolved in dry methylene chloride (20 mL) and cooled in an ice bath under Ar atmosphere. Trifluoroacetic anhydride (0.54 mL) and pyridine (0.5 mL) were added. After stirring at room temperature overnight the reaction mixture was hydrolyzed with aqueous solution of sodium bicarbonate, extracted with methylene chloride, washed with brine, dried over MgSO$_4$ and evaporated. Residue was purified on a silica gel column using a mixture of hexanes and methylene chloride to yield 0.068 g of trans-5,6,7,8,9,11,12-heptahydro-10-thia-3-hydroxy- 5-methyl-5,11-methanobenzocyclodecen-13-trifluoroacetamide.

Trans-5,6,7,8,9,11,12-heptahydro-10-thia-3-hydroxy-5-methyl-5,11-methanobenzocyclodecen-13-trifluoroacetamide was dissolved in a mixture of ethanol (2 mL) and water (1 mL) and then cooled in an ice bath. Monoperoxyphthalic acid, magnesium salt hexahydrate (0.21 g) was added. After 1 hour aqueous saturated sodium bicarbonate (5 mL) was added. Combined mixture was stirred at room temperature overnight and evaporated off and the residue extracted with methylene chloride. The latter solution was washed with brine and evaporated yielding 0.123 g trans-5,6,7,8,9,11,12-heptahydro-10-sulphono-3-hydroxy-5-methyl-5,11-methanobenzocyclodecen-13-trifluoroacetamide.

Trans-5,6,7,8,9,11,12-heptahydro-10-sulphono-3-hydroxy-5-methyl-5,11-methanobenzocyclodecen-13-trifluoroacetamide (0.123 g) was dried via azeotropic distillation with toluene and anhydrous hydrazine (2 mL) was added. The mixture was stirred at room temperature for 2 days then evaporated dried under vacuum. The product mixture was dissolved in methanol (2 mL) and allowed to stand at room temperature. Crystalline material (0.037 g) was filtered out and dissolved in a saturated solution of hydrogen chloride in methanol (2 mL) and then evaporated. The residue was lyophilized yielding 0.031 g of the title compound.

EXAMPLE 16

Time Course of the Neuroprotective Activity of the Compounds of the Invention For purposes of comparison, the compounds of the present invention and reference standards were administered to mice and the time course of neuroprotectant activity was determined subsequent to challenge by NMDA. Compounds were administered i.c.v. or i.p. at different times and concentrations prior to injection of NMDA (1 nmol/mouse, I.C.V.). The mortality rate (CD$_{50}$) TABLE I and the response curves.

Figure 1:
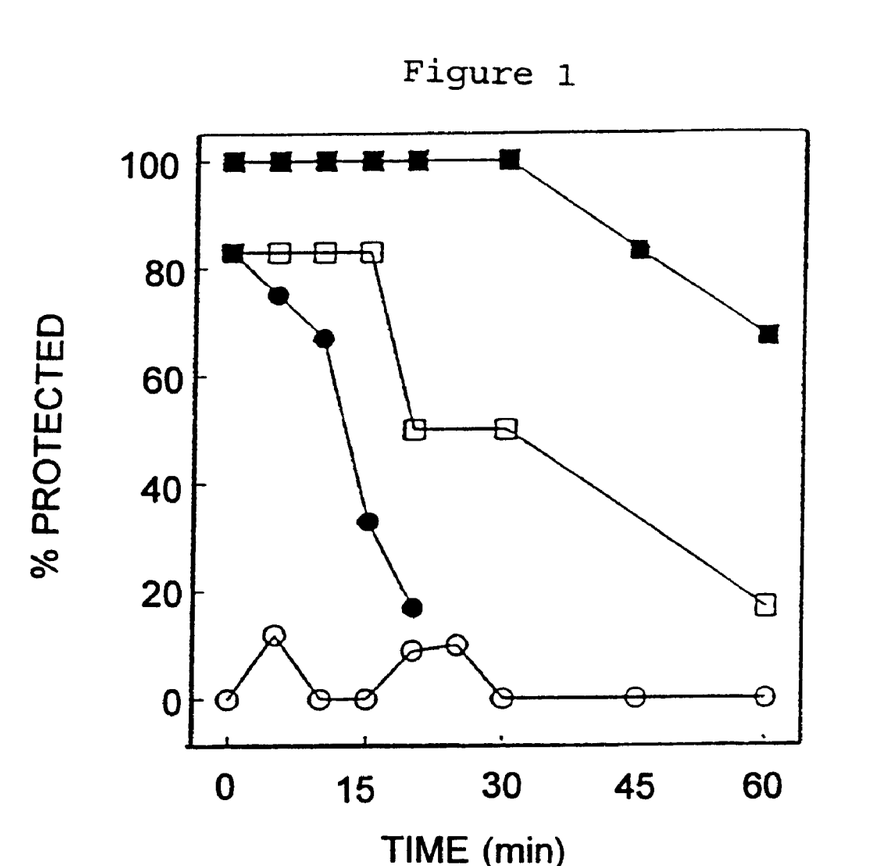
FIG. 1 depicts a dose dependent neuroprotectant activity effect of dextrorphan following NMDA challenge in mice.
Figure 2:
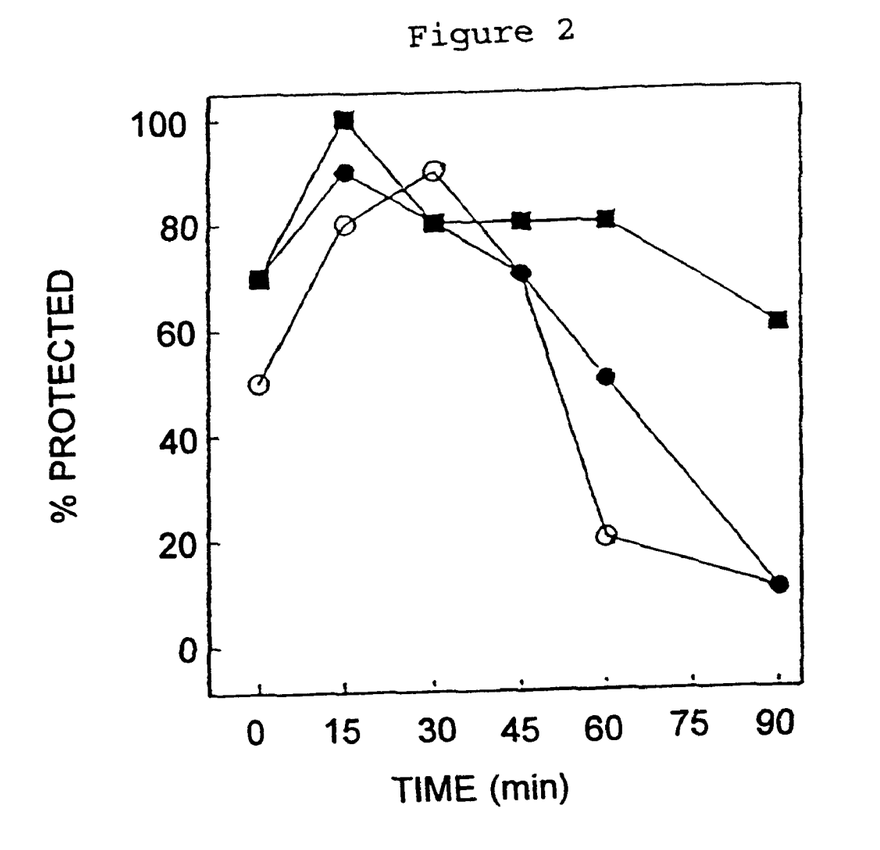
FIG. 2 depicts a dose dependent neuroprotectant activity effect of compound #13 following NMDA challenge in mice.
Figure 3:
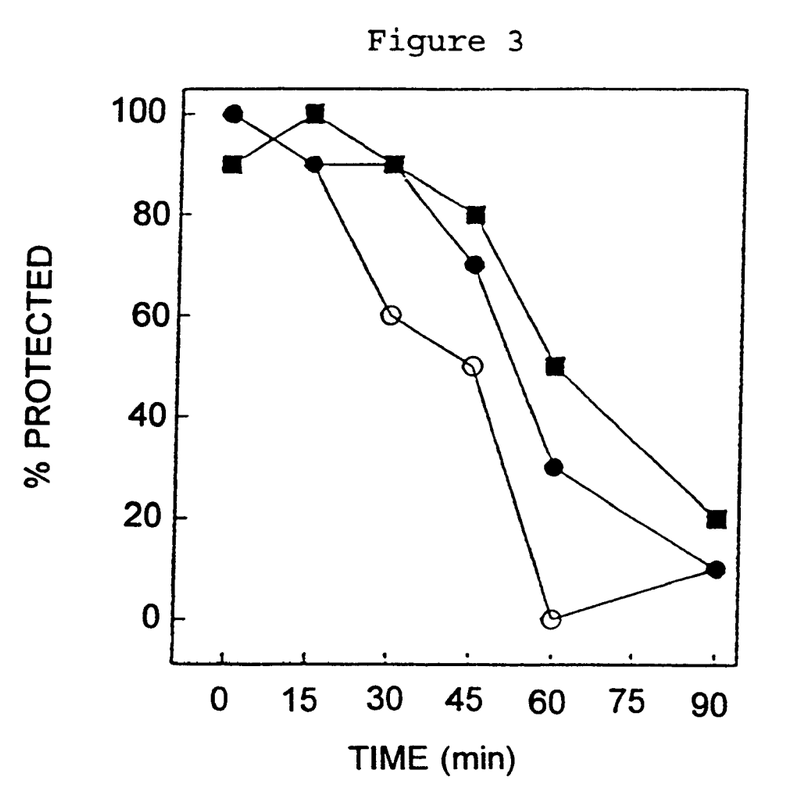
FIG. 3 depicts a dose dependent neuroprotectant activity effect of compound #9 following NMDA challenge in mice.

The results are presented in FIGS. 1, 2 and 3. FIG. 1 depicts a dose dependent neuroprotectant activity effect of dextrorphan following NMDA challenge in mice. The results demonstrate the time-dependent decreases in the protecting effects of the drug at various doses. In FIG. 1, dextrorphan was i.c.v. preadministered at a concentration of 1.0 (closed circle); 5.0 (open square); and 10 (closed square) nmole/mouse. The open circle represents preadministration of saline at a concentration of 10 μl/mouse.

A time course profile of the neuroprotectant activity of compound #13 in mice is presented in FIG. 2. The figure illustrates time-dependent decreases in the protecting effects of i.c.v. preadministration of compound #13 at varying dose against NMDA. A does dependent time course profile of the neuroprotectant activity against NMDA induced convulsions of compound #9 in mice is illustrated in FIG. 3. The graph illustrates time-dependent decreases in the protective effects of Compound #9 at various doses. In both FIGS. 2 and 3, the respective compound was preadministered at (open circle); 50 (closed circle); and 100 (closed square) nmole/mouse.

TABLE I

Comparison of anticonvulsant activity of compounds of the present invention and dextrorphan against NMDA-induced convulsions in mice (at 1 nmole/mouse)

| Compound | CD$_{50}$ nmol/mouse, icv (95% confidence interval) |
|---|---|
| Dextrorphan | 0.55 (0.39–0.78) |
| Compound #8b | 7.64 (4.8–12.0) |
| Compound #9 | 0.95 (0.62–1.45) |
| Compound #9a | 2.90 (1.75–4.85) |
| Compound #9b | 1.58 (0.95–2.62) |
| Compound #10 | 1.79 (0.99–3.25) |
| Compound #11 | 0.16 (0.11–0.25) |
| Compound #13 | 28.7 (15.3–53.8) |

Compounds of the invention demonstrated anticonvulsive activity against NMDA-induced convulsions in mice. Compound #11 demonstrated the greatest activity, possessing approximately 3 fold greater potency than Dextrorphan.

EXAMPLE 17

Motor Impairment

A. Locomotion and Falling Behaviour

Mice were place individually in observation cages for a 60 minute habituation period. They were injected I.C.V. with test compounds and observed for 15 to 30 minutes. Locomotion and falling behavior were assessed according to the procedure of Koek and Colpaert (J. Pharm. Exp. Therm. 252 349–357, 1990). For each animal, the presence of locomotor activity and falling behaviour was recorded. Statistical significance of drug-induced changes in the occurrence of a particular behaviour was tested by means of the method of Fray et al. (Psycopharmacol 69 253–259, 1980). MK-801, known to have intrinsic neurotoxicity, induced falling behaviour at doses as low as 1.5 nmol/mouse.

B. Assessment of Motor Coordination by Rotarod

Motor effects illicited by various antagonists were assessed using a rotarod treadmill (model 7600, UGO Basile, Italy). The method used was similar to the procedure described by Dunhamand Miya (J. Am. Pharmac. Assoc. 46 208–209–1957). The apparatus consisted of a rod of 2.5 cm diameter which was suspended horizontally 50 cm above a working area. The rod was turned at a speed of 8 rpm. Circular perplex separators were placed at intervals along the rod so that five animals could be tested simultaneously. All animals were conditioned to the rod for two consecutive days prior to experimentation.

The results of a study in which comparative motor impairment caused by Compound #13 was compared to dextrorphan, as assessed by rotarod. The percentage of animals showing motor effects is higher for animals treated with dextrorphan than for animals treated with Compound #13.

We claim:

1. A method of inhibiting NMDA receptor activation in a mammal comprising administering to said mammal an NMDA receptor antagonizing amount of a compound of formula (I):

formula I wherein R₁ is H, $C_{1-6}$ alkyl, or $C_{6-12}$ aryl optionally substituted with polar groups;

R₂ and R₃ are independently H, OH, $C_{1-6}$ alkyl, —C(NH)—NH₂, a positively charged group, or $C_{7-13}$ aralkyl optionally substituted with NH₂, OH, $C_{1-6}$ alky, or halogen; or R₂ and R₃ together form a 5 to 6 member ring optionally incorporating a heteroatom;

R₄ is H, $C_{1-6}$ alkyl, OR₆, SR₆, or N(R₆)₂, wherein each R₆ is independently H or $C_{1-3}$ alkyl;

X is O, S, SO, SO₂, or N—R₅, wherein each R₅ is independently H, $C_{1-6}$ alkyl, or $C_{7-13}$ aralkyl optionally interrupted with one or more heteroatom;

n is an integer from 0 to 2; and m is an integer from 0 to 3.

2. The method of claim 1, wherein X is S or SO₂, m is 3, and n is 0.

3. The method of claim 2, wherein X is S.

4. The method of claim 3, wherein R₂ is H, and R₃ is H, OH, or C(NH)—NH₂.

5. The method of claim 3, wherein R₁ is methyl.

6. The method of claim 3, wherein R₄ is OH or methoxy.

7. The method of claim 3, wherein R₄ is OH.

8. The method of claim 1, wherein the compound is 5,6,7,8,9,11,12-heptahydro-3-methoxy-5-methyl-10-thia-5,11-methanobenzocyclodecen-13-β-hydroxylamine (compound #8a); 5,6,7,8,9,11,12-heptahydro-3-methoxy-5-methyl-10-thia-5,11-methanobenzocyclodecen-13-amine (compound #8b); 5,6,7,8,9,11,12-heptahydro-3-hydroxy-5-methyl-10-thia-5,11-methanobenzocyclodecen-13-amine (sulphazocine) (compound #9); (−)-trans-5,6,7,8,9,11,12-heptahydro-10-thia-3-hydroxy-5-methyl-5,11-methanobenzocyclodecen-13-amine (compound #9a); (+)-trans-5,6,7,8,9,11,12-heptahydro-10-thia-3-hydroxy-5-methyl-5,11-methanobenzocyclodecen-13 amine (compound #9b); 5,6,7,8,9,11,12-heptahydro-3-hydroxy-5-methyl-10-thia-5,11-methanobenzocyclodecen-13-β-hydroxylamine (compound #10); trans-5,6,7,8,9,11,12-heptahydro-10-thia-3-hydroxy-5-methyl-5,11-methanobenzocyclodecen-13-guanidine (compound #11); or trans-5,6,7,8,9,11,12-heptahydro-10-sulphono-3-hydroxy-5-methyl-5,11-methanobenzocyclodecen-13-amine (compound #12).

9. The method of claim 1, wherein the compound is 5,6,7,8,9,11,12-heptahydro-3-hydroxy-5-methyl-10-thia-5,11-methanobenzocyclodecen-13-amine (sulphazocine) (compound #9); 5,6,7,8,9,11,12-heptahydro-3-hydroxy-5-methyl-10-thia-5,11-methanobenzocyclodecen-13-β-hydroxylamine (compound #10); or trans-5,6,7,8,9,11,12-heptahydro-10-thia-3-hydroxy-5-methyl-5,11-methanobenzocyclodecen-13-guanidine (compound #11).

10. The method of claim 1, wherein the compound is 5,6,7,8,9,11,12-heptahydro-3-hydroxy-5-methyl-10-thia-5,11-methanobenzocyclodecen-13-amine (sulphazocine) (compound #9).

11. The method of claim 1, wherein the compound is 5,6,7,8,9,11,12-heptahydro-3-hydroxy-5-methyl-10-thia-5,11-methanobenzocyclodecen-13-β-hydroxylamine (compound #10).

12. The method of claim 1, wherein the compound is trans-5,6,7,8,9,11,12-heptahydro-10-thia-3-hydroxy-5-methyl-5,11-methanobenzocyclodecen-13-guanidine (compound #11).

13. The method of claim 1, wherein said inhibition of NMDA receptor activation results in treating or preventing a condition selected from the group consisting of cell damage, neuronal cell damage, neurodegenerative disease, stroke, epileptic seizures, and convulsions.

14. The method of claim 13, wherein said neurodegenerative disease is selected from the group consisting of Alzheimer's disease, Huntington's disease, Parkinson's disease, and amyotrophic lateral sclerosis.

15. The method of claim 8, wherein said inhibition of NMDA receptor activation results in treating or preventing a condition selected from the group consisting of cell damage, neuronal cell damage, neurodegenerative disease, stroke, epileptic seizures, and convulsions.

16. The method of claim 9, wherein said inhibition of NMDA receptor activation results in treating or preventing a condition selected from the group consisting of cell damage, neuronal cell damage, neurodegenerative disease, stroke, epileptic seizures, and convulsions.

17. The method of claim 10, wherein said inhibition of NMDA receptor activation results in treating or preventing a condition selected from the group consisting of cell damage, neuronal cell damage, neurodegenerative disease, stroke, epileptic seizures, and convulsions.

18. The method of claim 11, wherein, said inhibition of NMDA receptor activation results in treating or preventing a condition selected from the group consisting of cell damage, neuronal cell damage, neurodegenerative disease, stroke, epileptic seizures, and convulsions.

19. The method of claim 12, wherein said inhibition of NMDA receptor activation results in treating or preventing a condition selected from the group consisting of cell damage, neuronal cell damage, neurodegenerative disease, stroke, epileptic seizures, and convulsions.

* * * * *